US00PP36449P2

(12) United States Plant Patent
Hartman

(10) Patent No.: US PP36,449 P2
(45) Date of Patent: Feb. 11, 2025

(54) ***CALADIUM* PLANT NAMED 'RUF OF18-231'**

(50) Latin Name: ***Caladium* X *hortulanum***
Varietal Denomination: RUF OF18-231

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 18/657,774

(22) Filed: May 7, 2024

(51) Int. Cl.
*A01H 5/12* (2018.01)
*A01H 6/10* (2018.01)

(52) U.S. Cl.
USPC ..... Plt./373
CPC ..... *A01H 6/10* (2018.05)

(58) Field of Classification Search
USPC ..... Plt./373
CPC ..... A01H 6/10; A01H 5/12
See application file for complete search history.

*Primary Examiner* — Keith O. Robinson
(74) *Attorney, Agent, or Firm* — C. Anne Whealy

(57) ABSTRACT

A new and distinct cultivar of *Caladium* plant named 'RUF OF18-231', characterized by its upright plant habit and short in height; compact, leafy and bushy appearance; vigorous growth habit and rapid growth rate; lance-type leaves that are dark green in color with red-colored venation and brighter red-colored interveinal areas with variable and random salmon pink or white-colored spots, flecks or speckles; and petioles that are pink in color with greenish brown-colored streaks, stippling and tessellations.

4 Drawing Sheets

Figure 1:
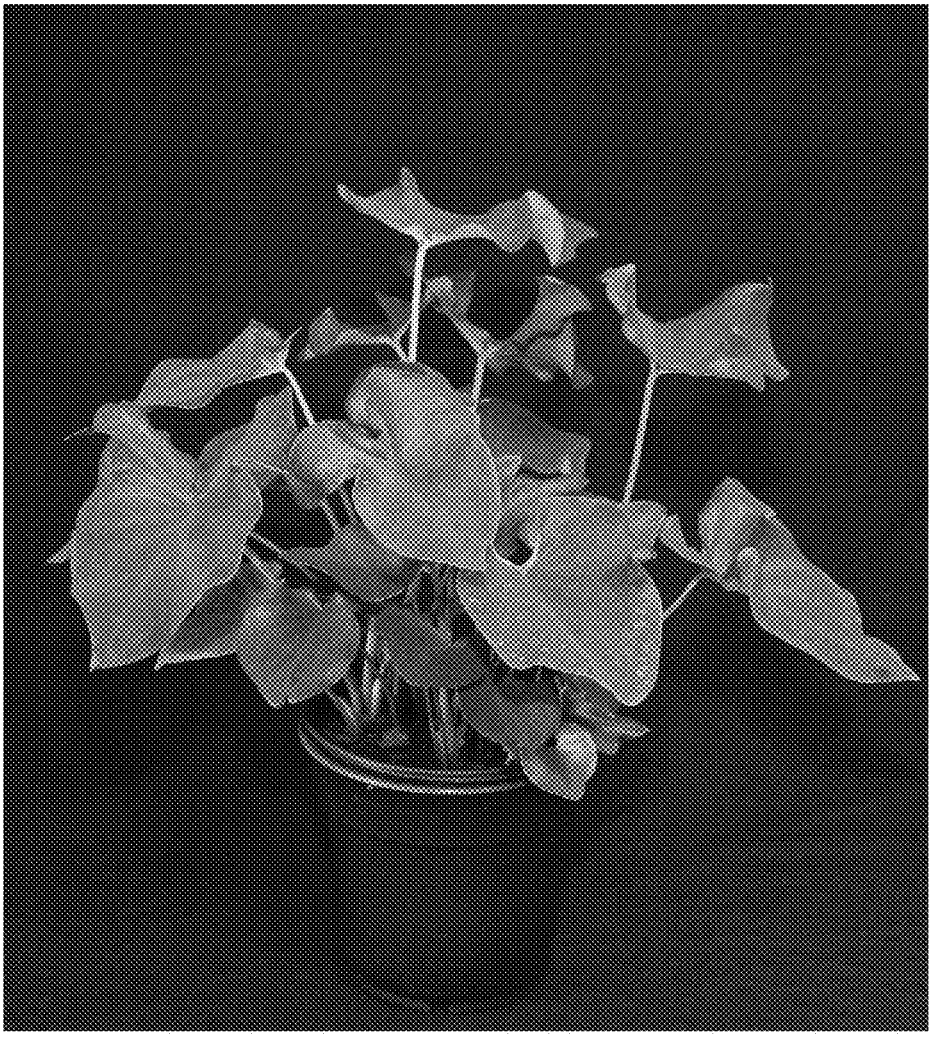

Botanical designation: *Caladium* X *hortulanum.*
Cultivar denomination: 'RUF OF18-231'.

BACKGROUND OF THE INVENTION

The present invention relates to a new and distinct cultivar of *Caladium* plant, botanically known as *Caladium X hortulanum,* commercially referred to as a lance leaf-type *Caladium* and hereinafter referred to by the name 'RUF OF18-231'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April 2017 in Avon Park, Florida of *Caladium* X *hortulanum* 'Flare', disclosed in U.S. Plant Pat. No. 25,426, as the female, or seed, parent with *Caladium* X *hortulanum* 'Red Flash', not patented, as the male, or pollen, parent. The new *Caladium* plant was discovered and selected by the Inventor as a single plant within the progeny of the stated cross-pollination in a controlled outdoor nursery environment in Avon Park, Florida in September 2018.

Asexual reproduction of the new *Caladium* plant by "chipping" the tubers (cutting the tuber into segments with each segment containing an axillary bud and tuber cortical tissue) in a controlled outdoor nursery environment in Zolfo Springs, Florida since April 2019 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'RUF OF18-231'. These characteristics in combination distinguish 'RUF OF18-231' as a new and distinct *Caladium* plant:

1. Upright plant habit and short in height; compact, leafy and bushy appearance.
2. Vigorous growth habit and rapid growth rate.
3. Lance-type leaves that are dark green in color with red-colored venation and brighter red-colored interveinal areas with variable and random salmon pink or white-colored spots, flecks or speckles.
4. Petioles that are pink in color with greenish brown-colored streaks, stippling and tessellations.

Plants of the new *Caladium* differ primarily from plants of the female parent, 'Flare', in the following characteristics:

1. Leaves of plants of the new *Caladium* are dark green in color with red-colored venation and brighter red-colored interveinal areas with variable and random salmon pink or white-colored spots, flecks or speckles whereas leaves of plants of 'Flare' have rose red-colored centers surrounded by greyed green and pink-colored speckling and dark green-colored margins.
2. Petioles of plants of the new *Caladium* are pink in color with greenish brown-colored streaks, stippling and tessellations whereas petioles of plants of 'Flare' are pink in color.

Plants of the new *Caladium* differ primarily from plants of the male parent, 'Red Flash', in the following characteristics:

1. Plants of the new *Caladium* are shorter and more compact than plants of 'Red Flash'.
2. Plants of the new *Caladium* grow faster than plants of 'Red Flash'.

3. Leaves of plants of the new *Caladium* are lance types whereas leaves of 'Red Flash' are fancy types.
4. Leaves of plants of the new *Caladium* are dark green in color with red-colored venation and brighter red-colored interveinal areas with variable and random salmon pink or white-colored spots, flecks or speckles whereas leaves of plants of 'Red Flash' have red-colored venation and interveinal areas with pink and white-colored spots and dark green-colored borders.
5. Petioles of plants of the new *Caladium* are pink in color with greenish brown-colored streaks, stippling and tessellations whereas petioles of plants of 'Red Flash' are reddish pink to tannish pink in color with dark brownish green-colored stippling and stripes.

Plants of the new *Caladium* can be compared to plants of *Caladium* X *hortulanum* 'Florida Red Ruffles', disclosed in U.S. Plant Pat. No. 13,136. In side-by-side comparisons, plants of the new *Caladium* differ primarily from plants of 'Florida Red Ruffles' in the following characteristics:

1. Leaves of plants of the new *Caladium* are dark green in color with red-colored venation and brighter red-colored interveinal areas with variable and random salmon pink or white-colored spots, flecks or speckles whereas leaves of plants of 'Florida Red Ruffles' have dark red-colored venation and interveinal areas and green-colored borders.
2. Petioles of plants of the new *Caladium* are pink in color with greenish brown-colored streaks, stippling and tessellations whereas petioles of plants of 'Florida Red Ruffles' are almost black in color with tannish pink-colored stripes.

Plants of the new *Caladium* can also be compared to plants of *Caladium* X *hortulanum* 'RUF 1522-3', disclosed in U.S. Plant Pat. No. 33,615. In side-by-side comparisons, plants of the new *Caladium* differ primarily from plants of 'RUF 1522-3' in the following characteristics:

1. Leaves of plants of the new *Caladium* are dark green in color with red-colored venation and brighter red-colored interveinal areas with variable and random salmon pink or white-colored spots, flecks or speckles whereas leaves of plants of 'RUF 1522-3' are dark red in color with dark green-colored margins.
2. Petioles of plants of the new *Caladium* are pink in color with greenish brown-colored streaks, stippling and tessellations whereas petioles of plants of 'RUF 1522-3' are tannish pink in color with greenish brown-colored stripes, streaks, stippling and tessellations.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet FIG. 1 is a side perspective view of a typical plant of 'RUF OF18-231' grown in a container that has had its tuber de-eyed prior to planting.

Figure 2:
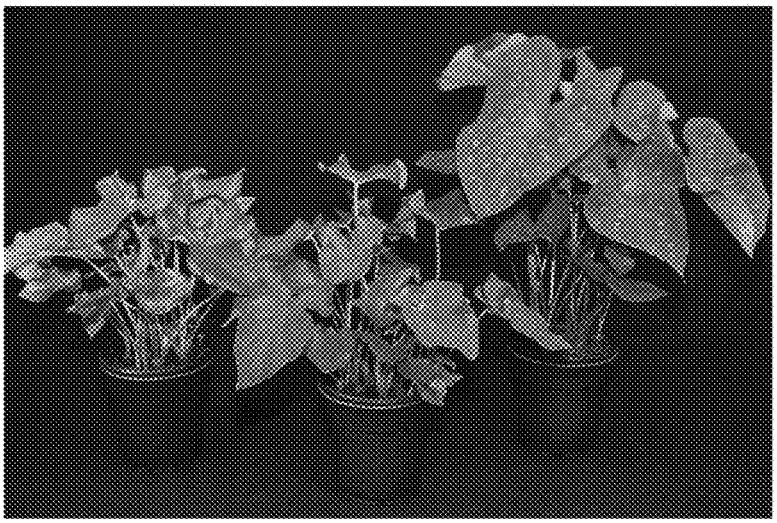

The photograph at the top of the second sheet FIG. 2 is side perspective view of typical plants of the female parent, 'Flare' (left), 'RUF OF18-231' (center) and the male parent, 'Red Flash' (right).

Figure 3:
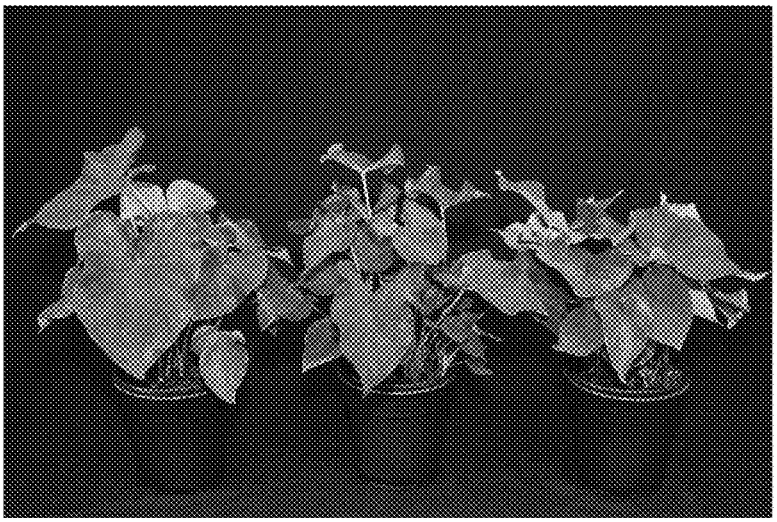

The photograph at the bottom of the second sheet FIG. 3 is side perspective view of typical plants of 'Florida Red Ruffles' (left), 'RUF OF18-231' (center) and 'RUF 1522-3' (right).

Figure 4:
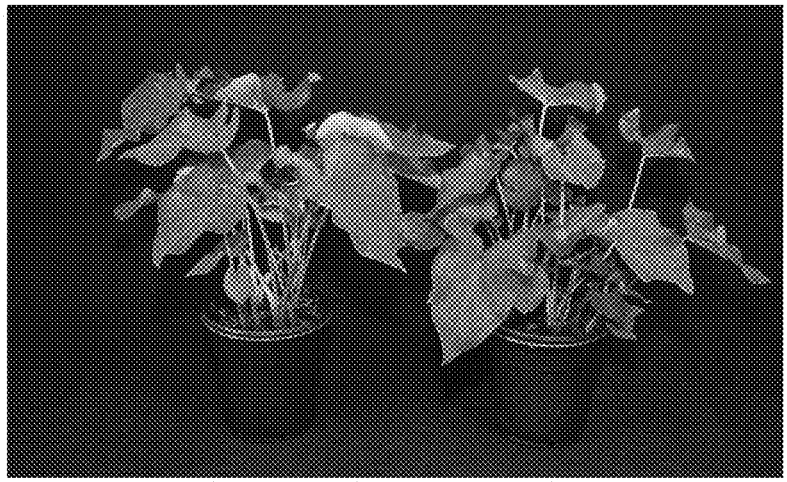

The photograph at the top of the third sheet FIG. 4 is a comparison view of typical plants of 'RUF OF18-231' grown in containers, the plant on the left has not had its tuber de-eyed and the plant on the right has had its tuber de-eyed prior to planting.

Figure 5:
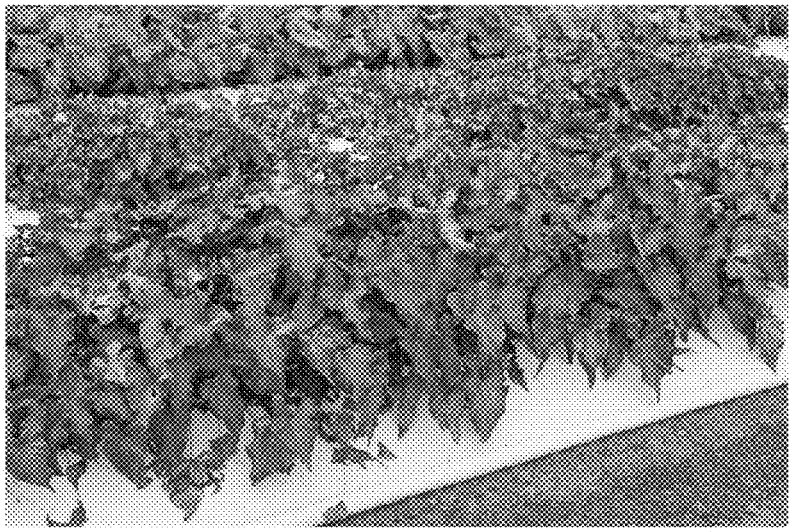

The photograph at the bottom of the third sheet FIG. 5 is a side perspective view of typical plants of 'RUF OF18-231' grown in an open production field.

Figure 6:
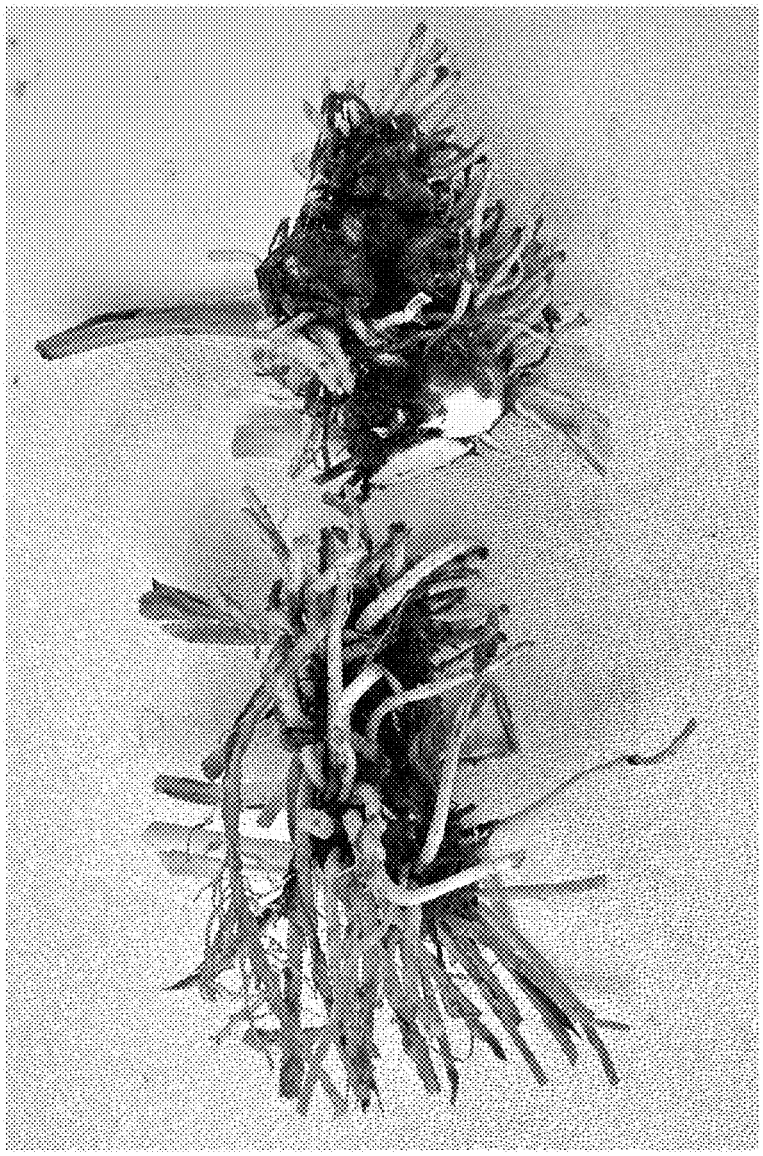

The photograph on the fourth sheet FIG. 6 is a close-up view of typical freshly-harvested tubers with roots of 'RUF OF18-231'.

DETAILED BOTANICAL DESCRIPTION

The aforementioned photographs and following observations and measurements describe plants grown in 15-cm containers in a polypropylene-covered shade house (30% light reduction) in Avon Park, Florida and plants grown in ground beds under full sunlight conditions in an outdoor nursery in Crewsville, Florida. The plants were grown under cultural practices typical of commercial shade house and outdoor nursery production. During the production of the shade house-grown plants, day temperatures ranged from about 28° C. to 33° C., night temperatures ranged from about 22° C. to 25° C. and light levels were about 1,300 μmol. During the production of the outdoor nursery-grown plants, day temperatures ranged from about 29° C. to 35° C., night temperatures ranged from about 23° C. to 26° C. and full sunlight conditions. Plants grown in the shade house were eight weeks old and plants grown in the outdoor nursery were seven months old when the photographs and the detailed description were taken. In the following description, color references are made to The Royal Horticultural Society Colour Chart, 2001 and 2015 Editions, except where general terms of ordinary dictionary significance are used.

Botanical classification: *Caladium* X *hortulanum* 'RUF OF18-231'.

Parentage:

*Female, or seed, parent.*—*Caladium* X *hortulanum* 'Flare', disclosed in U.S. Plant Pat. No. 25,426.

*Male, or pollen, parent.*—*Caladium* X *hortulanum* 'Red Flash', not patented.

Propagation:

*Type*.—By "chipping" the tubers.

*Time to initiate roots, summer*.—About seven to ten days at temperatures about 32° C.

*Time to initiate roots, winter*.—About two to three weeks at temperatures about 24° C.

*Tuber description* (*outdoor nursery-grown plants*).—Appearance: Multi-segmented and branched; individual segments are round to ovate or irregular in shape. Height: About 1.9 cm to 2.2 cm. Diameter: About 3 cm to 6.1 cm. Segment height: About 1.9 cm. Segment diameter: About 1.9 cm to 2.2 cm. Axillary bud shape: Roughly triangular to elliptic. Axillary bud height: About 2 mm. Axillary bud width: About 2 mm. Texture: Thick, starchy; somewhat brittle. Color: Periderm, freshly-harvested: Close to N199B. Periderm, dried: Close to 200A. Epidermis: Close to 158B to 158C flushed with close to N170D. Cortical tissue: Close to 4B to 4C. Axillary buds: Close to 38D. Root description: Relatively thick, fleshy contractile roots with few lateral branches; color, close to NN155C; actual color of the roots is dependent on substrate composition, water quality, fertilizer type and formulation, substrate temperature and physiological age of roots; root density, moderately dense.

Plant description:

*Plant type*.—Herbaceous perennial; suitable as a potted plant in containers 10-cm to 25-cm and suitable as a landscape plant in shaded areas.

*Plant and growth habit*.—Upright plant habit; short in height; compact, leafy and bushy appearance; vigorous growth habit and rapid growth rate; potted plants finish in saleable form in about six weeks after planting tubers; leaf petioles and leaves arise from one or more growing points on tubers; leaf petioles initially upright and leaning outwardly with development.

*Plant height, from soil level to top of foliar plane, shade house-grown potted plants*.—About 25 cm to 34 cm.

*Plant diameter, shade house-grown potted plants*.—About 38 cm to 55 cm.

*Number of shoots per plant, shade house-grown potted plants, tubers de-eyed*.—About five to seven develop per #1 tuber.

*Number of shoots per plant, shade house-grown potted plants, tubers not de-eyed*.—About three to four develop per #1 tuber.

*Cataphylls, shade house-grown potted plants*.—Length: About 4.5 cm. Width: About 6 mm. Shape: Lanceolate. Apex: Acute. Base: Sheathing the stem. Texture, outer and inner surfaces: Smooth, glabrous. Color, outer and inner surfaces: Close to 200B.

Leaf description:

*Arrangement and type*.—Alternate; simple; lance-type.

*Length, shade house-grown potted plants*.—About 15.5 cm to 19.5 cm.

*Width, shade house-grown potted plants*.—About 11 cm to 13 cm; flattened, about 11.5 cm to 14 cm.

*Shape*.—Ovate to lanceolate with cordate tendencies.

*Apex*.—Acute to acuminate.

*Base*.—Sagittate or sagittate-peltate, cordate.

*Margin*.—Entire; wavy with broad undulations.

*Texture and luster, upper surface*.—Smooth, glabrous; slightly glossy.

*Texture and luster, lower surface*.—Smooth, glabrous; glaucous; dull sheen.

*Venation pattern*.—Pinnate and palmate.

*Color, shade house-grown potted plants*.—When developing and fully expanded leaves, upper surface: Ground color: Close to 139A flushed with close to 183A; if present, random flecks, close to 180C to 180D. Marginal areas: Close to 139A or close to 180B tinged with close to 47C; edges, close to 187A; if present, random flecks, close to 180C to 180D and random spots, close to NN155D. Basal notch: Close to 187A and 139A. Midvein and lateral venation: Close to 46A; areas surrounding veins, close to 47A. When developing and fully expanded leaves, lower surface: Ground color: Close to 191A, 182C to 182D, 183A and/or 182B tinged with close to 48A; if present, random flecks, close to 182C to 182D. Marginal areas: Close to 191A; edges, close to 187A; if present, random flecks, close to 180C to 180D and random spots, close to NN155D. Basal notch: Close to 187A. Midvein: Close to 181D, 182A and/or 46A with streaks, close to 182A; areas surrounding veins, close to 184B. Lateral venation: Close to 182A and/or 196B to 196C with streaks, close to 182A; areas surrounding veins, close to 184B.

*Petioles*.—Aspect: Initially upright and straight and leaning outwardly with development; flexible. Length, shade house-grown potted plants: About 17 cm to 29.5 cm. Diameter, distally, shade house-grown potted plants: About 4.5 mm to 5.5 mm. Diameter, proximally, shade house-grown potted plants: About 5 mm to 7 mm. Texture: Smooth, glabrous; distally, glaucous, and proximally, slightly glossy. Color, shade house-grown potted plants: Close to 185D; variably streaked, close to 185B, 185C, 182D or 49D; variably stippled, close to 82C or 199D; tessellations, close to N200A; just below the leaf junction, close to 185D with streaks, close to 185B. Wing length, shade house-grown potted plants: About 4.5 cm to 9.9 cm. Wing diameter, shade house-grown potted plants: About 5 mm to 7 mm. Texture and luster, outer surface: Smooth, glabrous; slightly glossy. Texture and luster, inner surface: Smooth, glabrous; glossy. Wing color, shade house-grown potted plants: Outer surface: Close to 196D and 148A with streaks, stippling and tessellations, close to N199A and 147A. Inner surface: Close to NN155D; colors and patterns from the outer surface are visible on the inner surface.

Inflorescence description: To date, inflorescence development has not been observed on plants of the new *Caladium*.

Pathogen tolerance/resistance: Plants of the new *Caladium* have been observed to have average tolerance to *Pythium* Root Rot and average tolerance to *Xanthomonas* Leaf Spot. Plants of the new *Caladium* have not been observed to have tolerance/resistance to other pathogens common to *Caladium* plants.

Temperature tolerance: Plants of the new *Caladium* have been observed to tolerate temperatures ranging from about 7° C. to about 40° C. and are suitable for USDA Hardiness Zones 8A to 11. In cooler zones, tubers can be "lifted" prior to first freeze and stored in a cool dry environment to overwinter for re-planting the following spring.

It is claimed:

1. A new and distinct *Caladium* plant named 'RUF OF18-231' as illustrated and described herein.

* * * * *